United States Patent [19]

Tagnon

[11] 4,298,253

[45] Nov. 3, 1981

[54] METHOD AND APPARATUS FOR PRESENTING TEST IMAGES AT DIFFERENT DISTANCES FROM A SUBJECT

[75] Inventor: Luc A. Tagnon, Saint Mande, France

[73] Assignee: Essilor International, "Cie Generale d'Optique", Creteil, France

[21] Appl. No.: 81,149

[22] Filed: Oct. 2, 1979

[30] Foreign Application Priority Data

Oct. 5, 1978 [FR] France .................................. 78 28452

[51] Int. Cl.$^3$ ............................................... A61B 3/02
[52] U.S. Cl. ........................................ 351/17; 351/36; 351/39
[58] Field of Search ....................... 351/17, 36, 37, 39

[56] References Cited

U.S. PATENT DOCUMENTS 3,969,020  7/1976  Lynn et al. .............................. 351/17
4,179,196  12/1979  Persson et al. ..................... 351/36 X

FOREIGN PATENT DOCUMENTS 1061031  7/1959  Fed. Rep. of Germany .
1549385  10/1967  France .

Primary Examiner—John K. Corbin
Assistant Examiner—Rodney B. Bovernick
Attorney, Agent, or Firm—Charles E. Brown

[57] ABSTRACT

Method and apparatus for presenting test images to a subject at different distances and a constant visual angle. The test indicia are located at a single predetermined distance from the viewer. An optical system is provided between the test indicia and the viewer for including a lens system and at least one reflecting element or plane mirror. Displacements of the lens system along its optic axis and the plane mirror(s) along an axis parallel to a continuation of the lens system optic axis are coordinated so that the visual angle for the viewer remains the same regardless of the distance of the test image from the viewer. A single set of test indicia may be used for all potential image distances without having to vary the visual angle.

10 Claims, 5 Drawing Figures

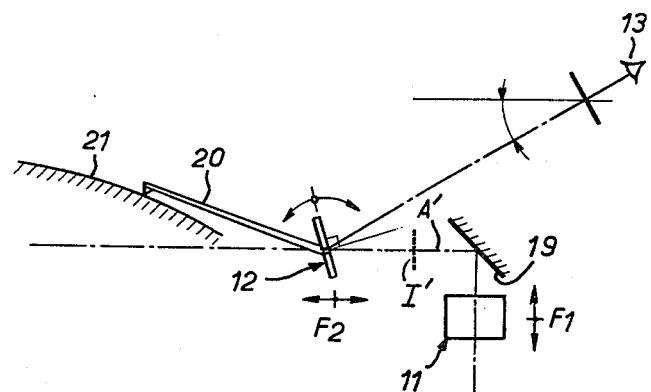
FIG.1
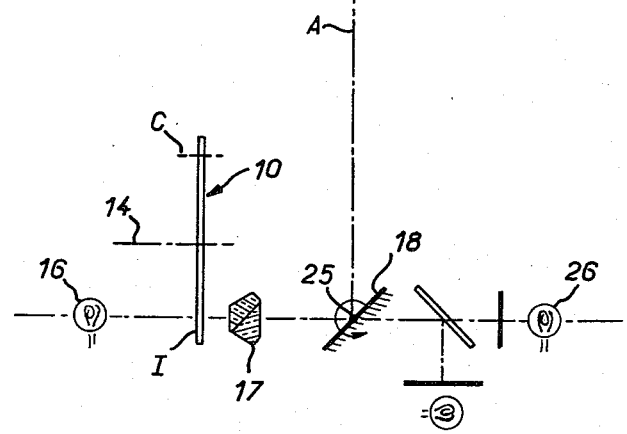
FIG.2
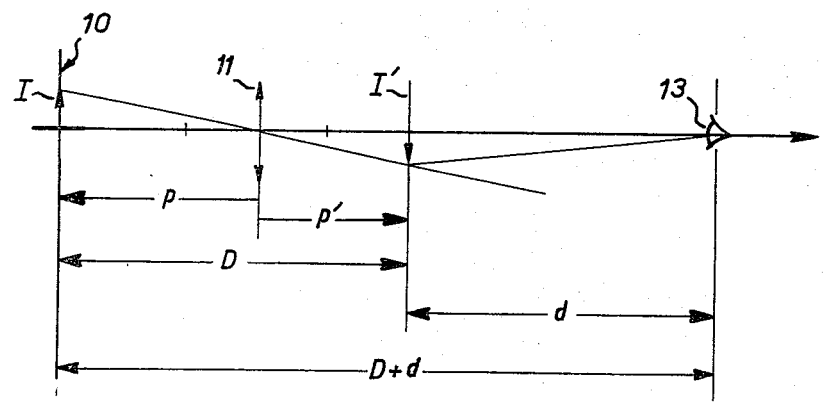

METHOD AND APPARATUS FOR PRESENTING TEST IMAGES AT DIFFERENT DISTANCES FROM A SUBJECT

BACKGROUND OF THE INVENTION

The present invention relates generally to the presentation of tests to a subject at different viewing distances, and more particularly to the presentation of eyesight tests, and especially those for checking the visual acuity of the subject.

Visual acuity tests are typically presented to the subject whose eyesight is to be checked at a single predetermined distance which corresponds, for example, to distant vision for the subject.

It would, however, also be interesting to be able to check the visual acuity of the subject for near vision, and intermediate vision, particularly for biotechnological purposes.

Such visual acuity testing at different distances typically involves successively placing the acuity test indicia at different distances from the subject between the shortest viewing distance and the longest viewing distance.

If in conjunction with such a change in viewing distances it is desirable to maintain the test indicia at the same visual acuity irrespective of the viewing distance it is normally necessary to have as many sets of different size test indicia as there are potential different viewing distances.

Indeed to maintain the visual acuity constant the visual angle under which the subject views the test images must remain constant and therefore the sizes of the test indicia increase proportionally to the viewing distance at which they are presented to the subject.

BRIEF SUMMARY OF THE INVENTION

A general object of the present invention is to provide a method and apparatus for presenting to a subject at different viewing distances various test images all at the same visual acuity, that is, all at the same visual angle, yet which only requires a single set of test indicia.

According to the invention there is provided a method and apparatus for presenting test indicia in which the test indicia are disposed at a single predetermined optical distance from the subject. The test indicia is presented to the subject through optical system including a lens system and at least one reflecting element which is adapted to form a visible test image for the subject. The reflecting element and the lens system are displaceable, and their displacements permit the distance from the test image to the subject to be varied. The displacements of the reflecting element and the lens system are coordinated so that as the distance from the test image to the subject and the magnification of the test are varied the visual angle for the subject remains constant.

The adjustment of the position of the reflecting element and the lens system as a function of the desired image distance may, if desired, be carried out manually. Alternatively, automatic coordinating means may be provided between the reflecting element and the lens system to achieve this result automatically.

Although the present method and apparatus are particularly well suited for the presentation of visual acuity tests, they may also present other tests, e.g. phoria tests. They are equally adapted to the determination of the subject's shortest viewing distance.

The features and advantages of the invention will be better understood from the description which follows, given by way of example, with reference to the accompanying schematic drawings.

BRIEF DESCRIPTION OF THE DRAWINGS

FIG. 1 is a schematic showing of an apparatus embodying the present invention;

FIG. 2 is an optical diagram illustrating the operation of the apparatus embodying the invention;

DETAILED DESCRIPTION OF THE PREFERRED EMBODIMENTS

Figure 3:
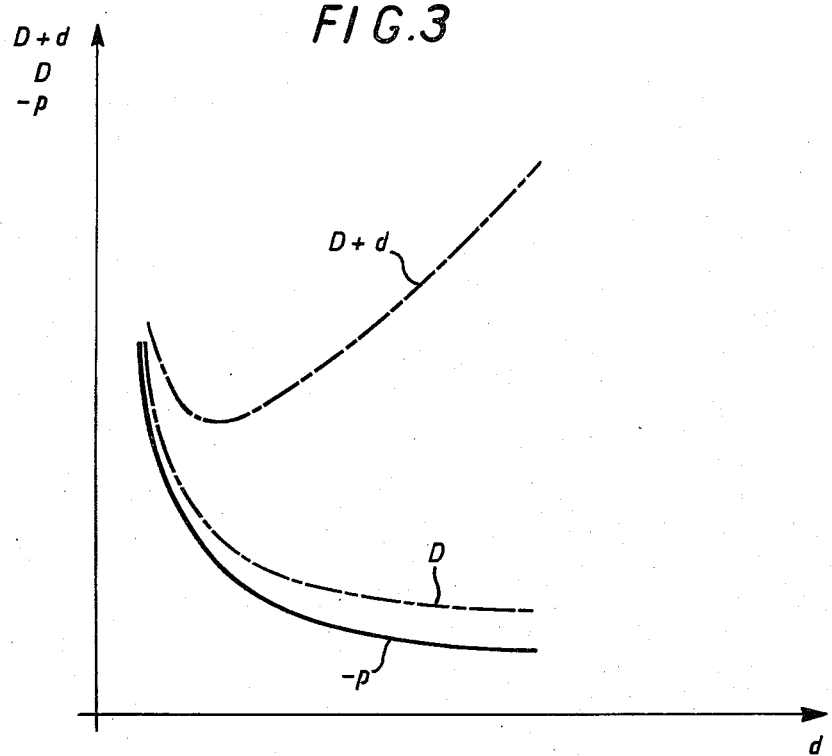
FIG. 3 is a graph illustrating the coordination of the adjustments of the lens system and the reflecting element.

As represented in the drawings, an apparatus according to the invention essentially comprises for the presentation of tests at different image distances from the subject or viewer, without a corresponding modification of the visual angle, a test holder disc or member 10, a lens system 11 adapted and arranged to form a test image I' of a test indicia I on the test holder disc 10 and a reflecting element 12 adapted to enable the subject, represented by a diagrammatic showing of his eye 13 in the drawings, to view test image I'.

In the embodiment illustrated in FIG. 1 the test holder disc 10 is a disc rotatably mounted about a horizontal axis 14 and provided with a plurality of acuity test indicia disposed along a circumference C at the outer periphery of the disc.

Preferably, the test indicia carried on the test holder disc 10 each correspond to different visual acuities.

The test indicia may be of any type whatever, for example, Landolt rings, i.e. black rings on a white background, or white rings on a black background, the rings having breaks which the subject has to locate.

In any event as test zones carried by the test holder disc 10 are transparent, a light source is provided facing a point along the circumference C on the test holder disc and, if need be, an attenuator.

Likewise, on the opposite side of the test holder disc 10 to the light source 16 is a Pechan prism 17 rotatably mounted about its axis and thereby adapted to turn the images of the Landolt rings or other indicia of the test zones carried by the test holder disc 10 around their centers.

Axis 14 of the test holder disc 10 is horizontal in the embodiment of FIG. 1 whereas the optic axis A of the lens system 11 is vertical. A mirror 18 which is oriented at 45° is provided to direct the rays of light from light source 16 emerging from test indicia I carried by test holder disc 10 and the Pechan prism onto lens system.

Similarly in the FIG. 1 embodiment a second mirror 19 oriented at a 45° angle is provided on the other side of the lens system between the latter and the reflecting element 12.

In any event, according to the invention the lens system 11 is movably mounted and adjustable in position along the optic axis A, in the directions of double-headed arrow $F_1$ in FIG. 1; the reflecting element 12 is movably mounted and adjustable in position along axis A' in the directions of double-headed arrow $F_2$. The direction of axis A' results from the change in direction of optic axis A caused by mirror 19 and therefore is the continuation of optic axis A.

In the illustrated embodiment of FIG. 1, the reflecting element 12 comprises a simple plane mirror oriented at an angle relative to axis A' along which it is adjustable in position. It is angularly adjustable about an axis perpendicular to axis A' so that regardless of its position along the axis A' the reflected rays are always directed towards the subject or viewer 13.

In the embodiment of FIG. 1 the mirror which the reflecting element 12 includes is rigidly fixed to an arm 20. To adjust the angular position of this mirror, the arm 20 is controlled by an appropriately profiled cam 21.

The actual physical structure of the various component parts will be a matter of design choice for those skilled in the art as is the case for the structure of the means for maintaining and/or controlling the component parts which means are not shown in detail in the drawings.

Reference will now be had to the optical diagram in FIG. 2 in which are represented the relative positions along the optic axis, which is assumed to be a straight line, of the test holder disc 10, and therefore test area including a test indicia I, the lens system 11, the test image I' of the test indicia I through the lens system 11 and the subject or viewer 13.

The distance d schematically represented in FIG. 2 between test image I' and the subject or viewer 13 is the image distance at which the image is viewed by the subject 13. As the subject or viewer 13, according to the invention, sees the image I' through the reflecting element 12 it is sufficient in order to vary the image distance d to displace the reflecting element 12 along the axis A'.

But it is necessary in conjunction therewith to displace the lens system 11 along the optic axis A in such a manner that the test image I' is indeed formed at the desired image distance d and its magnification is such that for the viewer or subject the visual angle remains constant regardless of the image distance.

The basic equation of the lens system 11 may be written as follows:

$$-\frac{1}{p} + \frac{1}{p'} = \frac{1}{f}$$

in which p is the distance of the lens system 11 from the test holder disc 10, p' is the distance of the test image I' from the lens system 11 and f is the focal distance of the lens system.

Letting g stand for the magnification, we have:

$$g = (p/p')$$

If the distance between the test image I' from the test holder disc 10 is designated by D we may write:

$$D = -p + p' = f\left(2 - g - \frac{1}{g}\right)$$

According to the invention it is proposed for an acuity test at a given visual angle for a selected reference image distance do to form another corresponding acuity test at the same acuity or visual angle but at an image distance d different from the reference image distance do.

Then the sizes of the test indicia in question must have a ratio which, equal to the magnification g imparted by the lens system 11, is equal to the ratio of the corresponding image distances, that is:

$$d/do = -g$$

Taking into account the foregoing relationships it is possible to calculate the value of D, and therefore p, as a function of the desired image distance:

$$D = f\left(2 - \frac{d}{do} + \frac{do}{d}\right) ; -p = \frac{D}{1 + \frac{d}{do}}$$

Thus, for each desired image distance d, it is possible to determine the value of the distance p at which the lens system 11 must be placed relative to the test carrier disc 10 in order that visual angle remain constant.

As illustrated in FIG. 3 a graph may be employed to this end.

In this graph which in effect coordinates the relative positions of the reflective element 12 and the lens system 11 to achieve the same acuity or visual angle in accordance with the invention, along the abscissa are marked the values of image distances d and along the ordinate are marked values corresponding to distances p, D and (D+d).

The curve representing the value of the distance p which is the most important distance, is in full line in FIG. 3, and the curves representing the distances D and (D+d) are illustrated in dash-dotted lines.

With this graph the user or operator may ascertain at any time, as a function of the selected image distance d, which enables the adjustment of the position of the reflecting element 12, the required position of the lens system 11.

Automatic coordinating means may of course be provided between the reflecting element 12 and the lens system 11. For example, the position of the reflecting element and the lens system along their respective axes of displacement may be controlled by suitable motor means, e.g. step-by-step or intermittent motors which together may be controlled by a programmer or a microprocessor. It then suffices to display on the programmer the desired image distance d to automatically adjust the positions of the lens system 11 and the reflecting element 12.

However it may be, when the test zones on the test carrier disc 10 are to be shown in succession corresponding to an image distance do at a given visual angle, the viewer 13 actually sees the succession of tests at a different image distance d which may be varied at will and advantageously, according to the invention, the tests image subtends the same angle at the viewer's eye irrespective of the selected image distance d.

Thus, a single family of test indicia is advantageously useable irrespective of the desired viewing distance.

Moreover, irrespective of the viewing distance the inter-test spacing advantageously remains constant.

Accordingly there is a simplification of the use of the results obtained with these tests.

But, as mentioned above, the apparatus according to the invention may also be used for presentation at different distances tests other than acuity tests. For example, as shown, it may serve as a phoria measurement at any distance. To this end there is provided in line with the circumference C on the test holder disc 10 but on the opposite side of the mirror 18 to the test carrier disc 10 a device 26 for measuring phorias; the mirror 18 is rocked around an axis lying in its plane so as to direct light rays emitted by the device 26 on the lens system 11 instead of those emerging from the test holder 10.

As the device 26 for measuring the phoria is known per se, and its details are not in themselves features of the present invention, it will not be described in greater detail herein.

Figure 4:
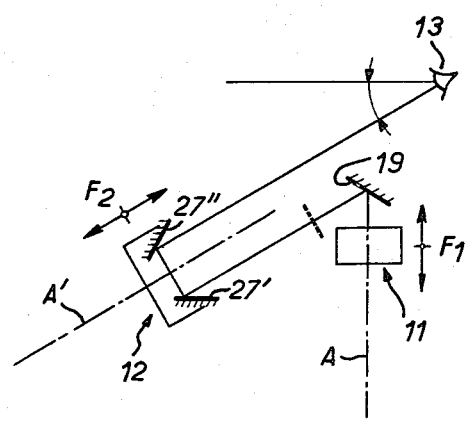
FIGS. 4 and 5 are views corresponding to a portion of FIGS. 1 and 2 illustrating a modified embodiment.

According to a modified embodiment illustrated in FIG. 4, the reflecting element 12 comprises two mirrors 27', 27" at 90° to each other but inclined in opposite directions at 45° relative to the axis A' along which the reflecting element is movably mounted and adjustable in position, the mirrors 27' and 27" being disposed on opposite sides of axis A'.

Such modified embodiment may advantageously maintain a constant orientation irrespective of its position along axis A'.

Figure 5:
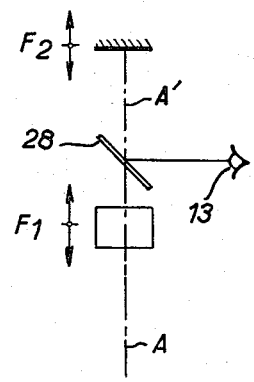

According to an alternative embodiment illustrated in FIG. 5 the reflecting element 12 comprises a plane mirror, which is perpendicular to axis A' relative to which it is adjustable in position, axis A' coinciding with opic axis A of the lens system 11, and a semi-transparent mirror 28 is interposed between the plane mirror and the lens system in line with the viewer 13.

The invention is not intended to be limited to the described and illustrated embodiments but encompasses without departing from the spirit and scope of the invention all variations, alternatives and expedients and combinations thereof.

In any event, according to the invention, the test indicia employed are disposed at a single predetermined physical distance from the subject or viewer, determined by the position of the test carrier disc relative to him, even though the test images are in fact presented to the subject at different image distances, bearing in mind that at each image distance d everything happens as though the test indicia presented is at a distance D+d different from the preceding physical distance and related to the image distance.

What I claim is:

1. In a method of presenting test images to a subject at different distances but for a constant visual acuity, in which the test indicia are located at a single predetermined optical distance from the subject, and an optical system is disposed between the test indicia and the subject including a lens system and a reflecting element for directing the test image towards the subject, the improvement comprising coordinating displacements of said reflecting element and said lens systems to vary the distance of the test image from the subject and the magnification of the test image so that the visual angle for the subject remains constant.

2. Apparatus for presenting test images to a subject at different distances but for a constant visual acuity, said apparatus comprising a test holder member, a lens system for forming an image of a test indicia carried by said test holder member, a reflecting element for directing the test image towards the subject, means for adjusting the position of said lens system along its optic axis, and means for adjusting the position of said reflecting element along an axis parallel to a continuation of said optic axis of said lens system, and means for coordinating the adjustment of the positions of said lens system and said reflecting element so as to maintain the visual angle for the subject constant.

3. Apparatus according to claim 2, wherein said reflecting element comprises a plane mirror.

4. Apparatus according to claim 3, wherein said means for adjusting the position of said reflecting element includes means for changing the angular inclination of said plane mirror, said plane mirror being normally maintained at an oblique angle relative to said axis parallel to said continuation of said optic axis.

5. Apparatus according to claim 3 wherein, said means for adjusting the position of said reflecting element comprises means for holding its position perpendicular to said axis parallel to said continuation of said optic axis.

6. Apparatus according to claim 2, wherein said reflecting element comprises two plane mirrors on opposite sides of said axis parallel to said continuation of said optic axis, each of said plane mirrors being inclined at 45° to said axis and at right angles to each other.

7. Apparatus according to claim 3, wherein said means for adjusting the position of said reflecting element includes means for changing the angular inclination of said plane mirror, in response to the adjusting of the position of said plane mirror.

8. Apparatus according to claim 7, wherein said means for changing the inclination of said plane mirror includes a cam.

9. Apparatus according to claim 7, wherein said means for changing the inclination of said plane mirror includes a fixed cam.

10. Apparatus according to claim 7, wherein said means for changing the inclination of said plane mirror includes a cam, and a follower for said cam fixedly secured to said plane mirror.

* * * * *